US011324396B2

(12) United States Patent
Yamazaki

(10) Patent No.: US 11,324,396 B2
(45) Date of Patent: May 10, 2022

(54) LIGHT SOURCE APPARATUS FOR ENDOSCOPE AND LIGHT-EMISSION AMOUNT CONTROL METHOD FOR THE SAME

(71) Applicant: OLYMPUS CORPORATION, Tokyo (JP)

(72) Inventor: Kenji Yamazaki, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 2 days.

(21) Appl. No.: 17/060,278

(22) Filed: Oct. 1, 2020

(65) Prior Publication Data

US 2021/0022592 A1   Jan. 28, 2021

Related U.S. Application Data

(63) Continuation of application No. PCT/JP2019/009750, filed on Mar. 11, 2019.

(30) Foreign Application Priority Data

Apr. 5, 2018  (JP) .............................. JP2018-073079

(51) Int. Cl.
*H04N 9/73* (2006.01)
*A61B 1/06* (2006.01)

(52) U.S. Cl.
CPC .............. *A61B 1/06* (2013.01); *H04N 9/735* (2013.01)

(58) Field of Classification Search
None
See application file for complete search history.

(56) References Cited

U.S. PATENT DOCUMENTS

2012/0075449 A1* 3/2012 Yasuda ................. A61B 1/0638
                                                              348/68
2014/0008672 A1* 1/2014 Takao ................. H01L 25/0753
                                                              257/89
(Continued)

FOREIGN PATENT DOCUMENTS

EP        3184879 A1    6/2017
EP        3202306 A1    8/2017
(Continued)

OTHER PUBLICATIONS

International Search Report dated Jun. 4, 2019 issued in PCT/JP2019/009750.

*Primary Examiner* — Eileen M Adams
(74) *Attorney, Agent, or Firm* — Scully, Scott, Murphy & Presser, P.C.

(57) ABSTRACT

In a light source apparatus for endoscope, when a light-emission amount of a second light source is less than or equal to a predetermined light-emission amount, a light source control circuit performs a first light-emission amount control of changing the light-emission amounts of the first to third light sources so as to allow a color balance to be maintained at a predetermined color balance. When the light-emission amount of the second light source is greater than the predetermined light-emission amount, the light source control circuit performs a second light-emission amount control of changing the light-emission amount of the third light source by a method different from the first light-emission amount control while changing the light-emission amounts of the first and second light sources by the same method as the first light-emission amount control so as to allow the color balance to be different from the predetermined color balance.

7 Claims, 4 Drawing Sheets

(56) References Cited

U.S. PATENT DOCUMENTS

| | | | |
|---|---|---|---|
| 2016/0143520 A1* | 5/2016 | Masaki | A61B 1/04 600/109 |
| 2017/0188803 A1 | 7/2017 | Yabe et al. | |
| 2017/0231480 A1 | 8/2017 | Yamazaki | |

FOREIGN PATENT DOCUMENTS

| | | |
|---|---|---|
| JP | 5401205 B2 | 1/2014 |
| JP | 2018-000228 A | 1/2018 |
| WO | WO 2016/059910 A1 | 4/2016 |
| WO | WO 2016/151903 A1 | 9/2016 |
| WO | WO 2018/003241 A1 | 1/2018 |

* cited by examiner

LIGHT SOURCE APPARATUS FOR ENDOSCOPE AND LIGHT-EMISSION AMOUNT CONTROL METHOD FOR THE SAME

CROSS REFERENCE TO RELATED APPLICATION

This application is a continuation application of PCT/JP2019/009750 filed on Mar. 11, 2019 and claims benefit of Japanese Application No. 2018-073079 filed in Japan on Apr. 5, 2018, the entire contents of which are incorporated herein by this reference.

BACKGROUND OF THE INVENTION

1. Field of the Invention

The present invention relates to a light source apparatus for endoscope, and in particular, to a light source apparatus for endoscope for use in observing living organism tissue, and a light-emission amount control method for the same.

2. Description of the Related Art

For endoscopic observation in the medical field, there has been conventionally known a technique of changing a color tone of illumination light for irradiating an object, such as living organism tissue in a subject, by changing the output light amount ratio among a plurality of light sources that generate light with different wavelengths.

More specifically, for example, Japanese Patent No. 5401205 discloses an endoscope apparatus including a plurality of types of light sources with different emission wavelengths, the endoscope apparatus being configured such that the output light amount ratio among the plurality of types of light sources is changed on the basis of approaching degree information on the approaching degree between the region to be observed of the subject and a distal end portion of an endoscope.

In endoscopic observation in the medical field, when the desired living organism tissue in a subject is irradiated with illumination light in the visible range, for example, a phenomenon may occur such that secondary light is generated due to reflection of the illumination light at a place different from the desired living organism tissue, and then, the desired living organism tissue is irradiated with the secondary light (together with the illumination light).

SUMMARY OF THE INVENTION

A light source apparatus for endoscope includes a first light source configured to generate blue light included in illumination light for irradiating living organism tissue in a subject, a second light source configured to generate green light included in the illumination light, a third light source configured to generate red light included in the illumination light; and a light source control unit configured to be capable of individually controlling a light-emitting state of each light source. When a light-emission amount of the second light source is less than or equal to a predetermined light-emission amount, the light source control unit performs a first light-emission amount control of changing light-emission amounts of the first light source, the second light source, and the third light source so as to allow a color balance of light of each color included in the illumination light to be maintained at a predetermined color balance, and when the light-emission amount of the second light source is greater than the predetermined light-emission amount, the light source control unit performs a second light-emission amount control of changing the light-emission amount of the third light source by a method different from the first light-emission amount control while changing the light-emission amounts of the first light source and the second light source by a method similar to the first light-emission amount control so as to allow the color balance of light of each color included in the illumination light to be different from the predetermined color balance.

A light-emission amount control method for the light source apparatus for endoscope according to an aspect of the present invention is adapted to individually control light-emitting states of a first light source configured to generate blue light included in illumination light for irradiating living organism tissue in a subject, a second light source configured to generate green light included in the illumination light, and a third light source configured to generate red light included in the illumination light. The method includes performing, when a light-emission amount of the second light source is less than or equal to a predetermined light-emission amount, a first light-emission amount control of changing light-emission amounts of the first light source, the second light source, and the third light source so as to allow a color balance of light of each color included in the illumination light to be maintained at a predetermined color balance, and performing, when the light-emission amount of the second light source is greater than the predetermined light-emission amount, a second light-emission amount control of changing the light-emission amount of the third light source by a method different from the first light-emission amount control while changing the light-emission amounts of the first light source and the second light source by a method similar to the first light-emission amount control so as to allow the color balance of light of each color included in the illumination light to be different from the predetermined color balance.

DETAILED DESCRIPTION OF THE PREFERRED EMBODIMENTS

Hereinafter, embodiments of the present invention will be described with reference to the drawings.

FIGS. 1 to 6 are related to the embodiments of the present invention.

Figure 1:
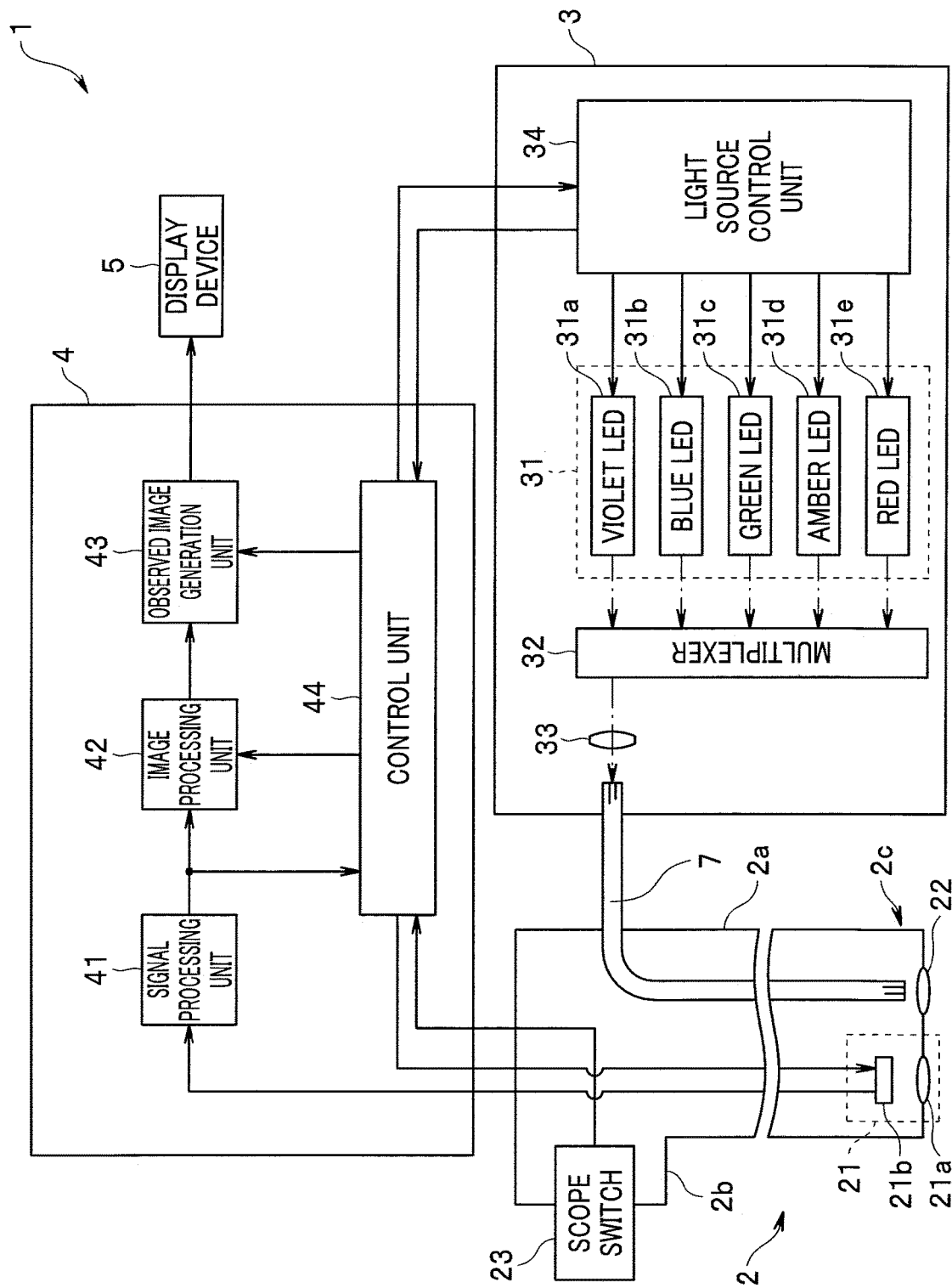
FIG. 1 is a view illustrating a configuration of a main portion of an endoscope system according to an embodiment.

An endoscope system 1 includes, as illustrated in FIG. 1, an endoscope 2 that can be inserted into a subject and is configured to pick up an image of an object, such as living organism tissue in the subject, and output a resulting image pickup signal; a light source apparatus 3 configured to supply illumination light for use in observing the object via a light guide 7 inserted through and disposed in the endoscope 2; a processor 4 configured to generate an observed image and the like corresponding to the image pickup signal outputted from the endoscope 2, and output the observed image; and a display device 5 configured to display on a screen the observed image outputted from the processor 4. FIG. 1 is a view illustrating a configuration of a main portion of the endoscope system according to an embodiment.

The endoscope 2 includes an insertion portion 2a formed in an elongated shape so as to be insertable into a subject, and an operation portion 2b provided on a proximal end side of the insertion portion 2a. The endoscope 2 is configured to be detachably connected to the processor 4 via a universal cable (not illustrated) incorporating a signal wire used for transmission of various signals, such as an image pickup signal outputted from an image pickup unit 21 (described below). The endoscope 2 is also configured to be detachably connected to the light source apparatus 3 via a light guide cable (not illustrated) incorporating at least a part of the light guide 7.

A distal end portion 2c of the insertion portion 2a is provided with the image pickup unit 21 for picking up an image of an object, such as living organism tissue in a subject, an output end portion of the light guide 7, and an illumination optical system 22 for irradiating the object with illumination light transmitted through the light guide 7.

The image pickup unit 21 is configured to pick up an image of return light from the object irradiated with illumination light from the illumination optical system 22, and output the resulting image pickup signal. More specifically, the image pickup unit 21 includes an objective optical system 21a configured to form an image of return light generated from the object irradiated with illumination light from the illumination optical system 22, and an image pickup device 21b configured to pick up the image of the return light formed by the objective optical system 21a so as to generate an image pickup signal, and output the generated image pickup signal to the processor 4.

The image pickup device 21b includes an image sensor, such as a CCD or a CMOS. An image pickup plane of the image pickup device 21b is provided with color filters in a Bayer arrangement of primary colors, for splitting the return light received from the objective optical system 21a into three colors of red, green, and blue, and a plurality of pixels arranged in matrix for picking up an image of the light having passed through the color filters. The image pickup device 21b is configured to perform an operation according to a control signal outputted from the processor 4.

The operation portion 2b has a shape that allows a user to grip and operate the operation portion 2b. The operation portion 2b is provided with a scope switch 23 including one or more switches capable of issuing an instruction to the processor 4 in response to an input operation by the user.

The light source apparatus 3 is configured as a light source apparatus for endoscope that supplies illumination light to the endoscope 2. The light source apparatus 3 includes a light-emitting unit 31, a multiplexer 32, a condenser lens 33, and a light source control unit 34.

The light-emitting unit 31 includes a violet LED 31a, a blue LED 31b, a green LED 31c, an amber LED 31d, and a red LED 31e. In other words, the light-emitting unit 31 includes a plurality of semiconductor light-emitting elements. Each LED of the light-emitting unit 31 is configured to individually emit or quench light as controlled by the light source control unit 34. Each LED of the light-emitting unit 31 is also configured to emit light with a light-emission amount as controlled by the light source control unit 34.

Figure 2:
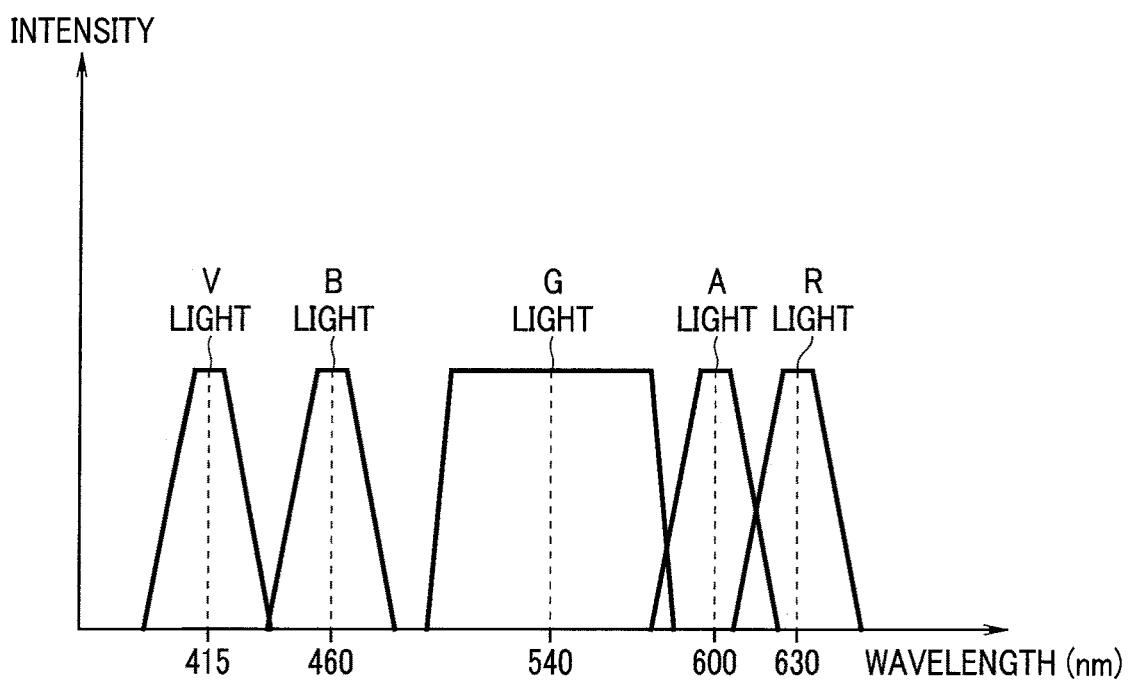
FIG. 2 is a view illustrating an exemplary wavelength range of light emitted from each LED provided in a light source apparatus according to the embodiment.

The violet LED 31a is configured to generate violet light (hereinafter referred to as V light) having the center wavelength in the violet range. More specifically, the violet LED 31a is configured to generate light with the center wavelength set around 415 nm as the V light as illustrated in FIG. 2, for example. Note that a light-emission amount EV of the violet LED 31a is defined as the total amount of light obtained by integrating the intensity of light with each wavelength included in the wavelength range of the V light. FIG. 2 is a view illustrating an exemplary wavelength range of light emitted from each LED provided in the light source apparatus according to the embodiment.

The blue LED 31b is configured to generate blue light (hereinafter referred to as B light) having the center wavelength in the blue range on the longer wavelength side with respect to the wavelength of the V light. More specifically, the blue LED 31b is configured to generate light with the center wavelength set around 460 nm as the B light as illustrated in FIG. 2, for example. Note that a light-emission amount EB of the blue LED 31b is defined as a total amount of light obtained by integrating the intensity of light with each wavelength included in the wavelength range of the B light.

The green LED 31c is configured to generate green light (hereinafter referred to as G light) having the center wavelength in the green range on the longer wavelength side with respect to the wavelength of the B light. More specifically, the green LED 31c is configured to generate light with the center wavelength set around 540 nm as the G light as illustrated in FIG. 2, for example. It should be noted that a light-emission amount EG of the green LED 31c is defined as a total amount of light obtained by integrating the intensity of light with each wavelength included in the wavelength range of the G light.

The amber LED 31d is configured to generate amber light (hereinafter referred to as A light) having the center wavelength in the amber range on the longer wavelength side with respect to the wavelength of the G light. More specifically, the amber LED 31d is configured to generate light with the center wavelength set around 600 nm as the A light as illustrated in FIG. 2, for example. Note that a light-emission amount EA of the amber LED 31d is defined as a total amount of light obtained by integrating the intensity of light with each wavelength included in the wavelength range of the A light.

The red LED 31e is configured to generate red light (hereinafter referred to as R light) having the center wavelength in the red range on the longer wavelength side with respect to the wavelength of the A light. More specifically, the red LED 31e is configured to generate light with the center wavelength set around 630 nm as the R light as illustrated in FIG. 2, for example. Note that a light-emission amount ER of the red LED 31e is defined as a total amount of light obtained by integrating the intensity of light with each wavelength included in the wavelength range of the R light.

The multiplexer 32 is configured to multiplex each light emitted from the light-emitting unit 31 and make the resulting light beam incident on the condenser lens 33.

The condenser lens 33 is configured to focus the light received through the multiplexer 32 and output the resulting focused light to an input end portion of the light guide 7.

The light source control unit 34 includes a control circuit, for example. The light source control unit 34 is configured to perform an operation to obtain a current light-emission amount EGC of the green LED 31c. The light source control unit 34 is also configured to be capable of individually controlling a light-emitting state of each LED of the light-emitting unit 31 based on a control signal outputted from the processor 4 and the current light-emission amount EGC of the green LED 31c. The light source control unit 34 is also configured to generate a light-emitting state signal indicating the light-emitting state of each LED of the light-emitting unit 31 and output the signal to a control unit 44. A specific example of the operation performed by the light source control unit 34 will be described later.

In other words, the light source apparatus 3 includes the violet LED 31a configured to generate the V light included in the illumination light for irradiating living organism tissue in a subject, the blue LED 31b configured to generate the B light included in the illumination light, the green LED 31c configured to generate the G light included in the illumination light, the amber LED 31d configured to generate the A light included in the illumination light, and the red LED 31e configured to generate R light included in the illumination light.

The processor 4 includes a signal processing unit 41, an image processing unit 42, an observed image generation unit 43, and the control unit 44.

The signal processing unit 41 includes a signal processing circuit, for example. The signal processing unit 41 is configured to perform predetermined signal processing, such as A/D conversion, on an image pickup signal outputted from the endoscope 2 so as to generate image data, and output the generated image data to each of the image processing unit 42 and the control unit 44 frame by frame.

The image processing unit 42 includes an image processing circuit, for example. The image processing unit 42 is configured to, based on the image data outputted from the signal processing unit 41 and a control signal outputted from the control unit 44, perform a process for generating each of image data IDV of violet components corresponding to the V light included in the return light of the illumination light that has irradiated the object and image-picked-up through a B (blue) filter of the image pickup device 21b, and image data IDB of blue components corresponding to the B light included in the return light and image-picked-up through the B filter. The image processing unit 42 is also configured to, based on the image data outputted from the signal processing unit 41 and a control signal outputted from the control unit 44, perform a process for generating image data IDG of green components corresponding to the G light included in the return light of the illumination light that has irradiated the object and image-picked-up through a G (green) filter of the image pickup device 21b. The image processing unit 42 is also configured to, based on the image data outputted from the signal processing unit 41 and a control signal outputted from the control unit 44, perform the process for generating each of image data IDA of amber components corresponding to A light included in the return light of the illumination light that has irradiated the object and image-picked-up through an R (red) filter of the image pickup device 21b and image data IDR of red components corresponding the R light included in the return light and image-picked-up through the R filter. In addition, the image processing unit 42 is configured to perform predetermined image processing on the image data of each color component generated as described above and output the processing results to the observed image generation unit 43.

The observed image generation unit 43 includes an image generation circuit, for example. The observed image generation unit 43 is configured to generate an observed image using the image data outputted from the image processing unit 42 based on a control signal outputted from the control unit 44, and output the generated observed image to the display device 5 frame by frame.

The control unit 44 includes a control circuit, for example. The control unit 44 is configured to generate a control signal for performing an operation according to an instruction from the scope switch 23 and output the control signal. The control unit 44 is also configured to generate a control signal for controlling an operation of the image pickup device 21b and output the control signal.

The control unit 44 is configured to perform a brightness detection process for detecting the current brightness of the image data outputted from the signal processing unit 41. The control unit 44 is also configured to generate a control signal for performing a dimming operation to bring the current brightness, which has been obtained as a result of performing the aforementioned brightness detection process, closer to a predetermined brightness, and output the control signal to the light source control unit 34.

The control unit 44 is configured to generate a control signal for performing an operation according to the light-emitting state signal outputted from the light source control unit 34 and output the control signal to each of the image processing unit 42 and the observed image generation unit 43.

In the present embodiment, each unit of the processor 4 may be configured as, for example, an individual electronic circuit or a circuit block of an integrated circuit, such as an FPGA (field programmable gate array). In the present embodiment, the processor 4 may include one or more CPUs, for example. Alternatively, the configuration according to the present embodiment may be appropriately modified to allow the processor 4 to read from a storage medium (not illustrated), such as a memory, programs for executing the functions of the signal processing unit 41, the image processing unit 42, the observed image generation unit 43, and the control unit 44, and perform operations according to the read programs, for example.

The display device 5 includes an LCD (liquid crystal display), for example, and is configured to be capable of displaying an observed image and the like outputted from the processor 4.

Next, an operation of the present embodiment will be described below.

A user connects each unit of the endoscope system 1 and turns on power, and then inserts the insertion portion 2a into an examinee while checking an observed image displayed on the display device 5, and also disposes the distal end portion 2c at a position where a desired living organism tissue in the examinee is located within an observation field of view of the objective optical system 21a.

If the current brightness obtained by performing the brightness detection process on the image data outputted from the signal processing unit 41 is less than the predetermined brightness, the control unit 44 generates a control signal CSA for increasing the amount of the illumination light supplied from the light source apparatus 3 to the endoscope 2 from a current amount of light and outputs the signal to the light source control unit 34. If the current brightness obtained by performing the brightness detection process on the image data outputted from the signal processing unit 41 is greater than the predetermined brightness, the control unit 44 generates a control signal CSB for reducing the amount of the illumination light supplied from the light source apparatus 3 to the endoscope 2 from the current amount of light, and outputs the signal to the light source control unit 34. If the current brightness obtained by performing the brightness detection process on the image data outputted from the signal processing unit 41 coincides with the predetermined brightness, the control unit 44 generates a control signal for maintaining the amount of the illumination light supplied from the light source apparatus 3 to the endoscope 2 at the current amount of light, and outputs the signal to the light source control unit 34.

The light source control unit 34 controls the light-emitting state of each LED of the light-emitting unit 31 based on a control signal outputted from the control unit 44 and the current light-emission amount EGC of the green LED 31c.

Figure 3:
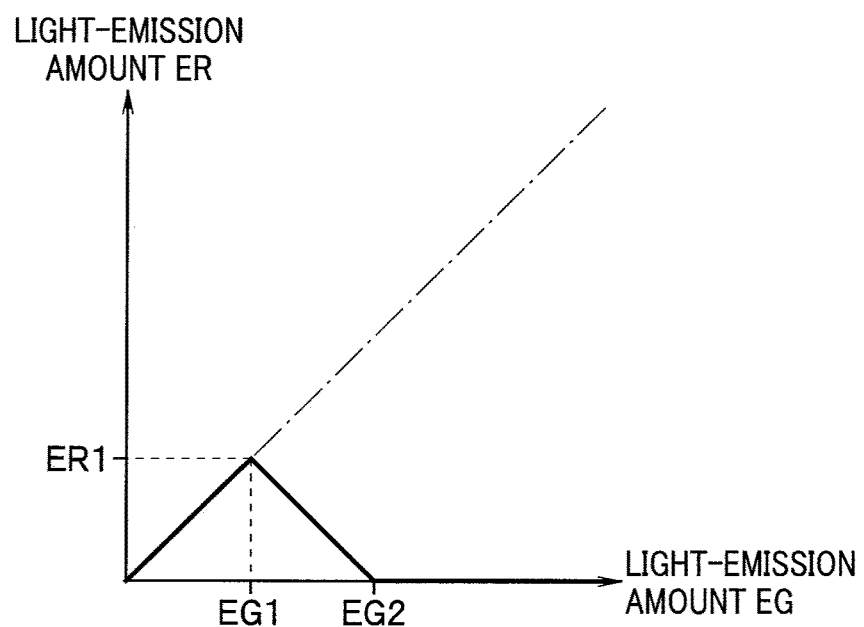
FIG. 3 is a view for illustrating an operation of the light source apparatus according to the embodiment.
Figure 4:
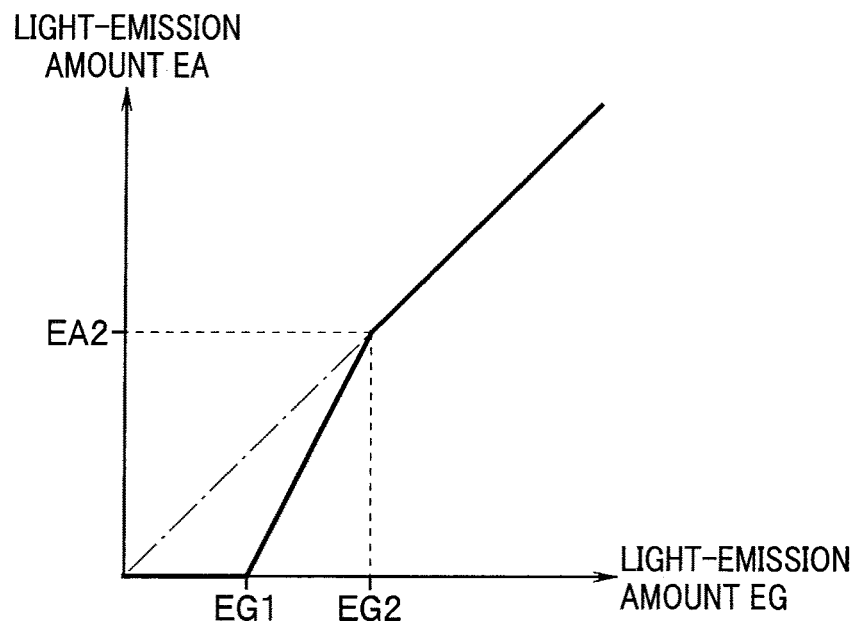
FIG. 4 is a view for illustrating an operation of the light source apparatus according to an embodiment.

Hereinafter, an example of a specific operation performed by the light source control unit 34 and the like will be described with reference to FIGS. 3 and 4, for example. FIGS. 3 and 4 are views for illustrating the operation of the light source apparatus according to the embodiment.

Described first is an operation performed when the current light-emission amount EGC of the green LED 31c is greater than zero and less than or equal to a light-emission amount EG1, that is, when the observation distance between the distal end portion 2c and the desired living organism tissue is a distance corresponding to a near view. A specific example of a method of setting the light-emission amount EG1 will be described later.

The light source control unit 34 controls the light-emitting unit 31 to concurrently light the violet LED 31a, the blue LED 31b, the green LED 31c, and the red LED 31e while quenching the amber LED 31d, and then generates a light-emitting state signal according to such control and outputs the signal to the control unit 44. According to such operation of the light source control unit 34, mixed light of the V light, the B light, the G light, and the R light is allowed to irradiate the desired living organism tissue as the illumination light when the observation distance between the distal end portion 2c and the desired living organism tissue is a distance corresponding to the near view.

The light source control unit 34 also controls the light-emitting unit 31 to change the light-emission amount EV, the light-emission amount EB, the light-emission amount EG, and the light-emission amount ER while maintaining a preset light-emission amount ratio among these light-emission amounts.

More specifically, for example, when the light-emission amount ratio among the light-emission amount EV, the light-emission amount EB, the light-emission amount EG, and the light-emission amount ER is set to 1:1:1:1, the light source control unit 34, when receiving the control signal CSA, controls the light-emitting unit 31 to linearly increase the four light-emission amounts while maintaining EV=EB=EG=ER (see FIG. 3). In addition, for example, when the light-emission amount ratio among the light-emission amount EV, the light-emission amount EB, the light-emission amount EG, and the light-emission amount ER is set to 1:1:1:1, the light source control unit 34, when receiving the control signal CSB, controls the light-emitting unit 31 to linearly decrease the four light-emission amounts while maintaining EV=EB=EG=ER (see FIG. 3).

Note that the alternate long and short dash line in FIG. 3 indicates changes in the light-emission amount when EG=ER. Therefore, when the control illustrated in the graph of FIG. 3 is performed, a relationship of EG1=ER1 is satisfied.

The image processing unit 42 performs a process for generating each of the image data IDV, the image data IDB, the image data IDG, and the image data IDR based on image data outputted from the signal processing unit 41 and a control signal outputted from the control unit 44 according to the aforementioned operation of the light source control unit 34.

The observed image generation unit 43, based on a control signal outputted from the control unit 44, generates an observed image by assigning the image data IDV and the image data IDB outputted from the image processing unit 42 to a B (blue) channel of the display device 5, assigning the image data IDG outputted from the image processing unit 42 to a G (green) channel of the display device 5, and assigning the image data IDR outputted from the image processing unit 42 to an R (red) channel of the display device 5, and then outputs the generated observed image to the display device 5.

Described next is an operation performed when the current light-emission amount EGC of the green LED 31c is greater than the light-emission amount EG1 and less than a light-emission amount EG2, that is, when the observation distance between the distal end portion 2c and the desired living organism tissue is a distance corresponding to a middle-distance view. A specific example of a method of setting the light-emission amount EG2 will be described later.

The light source control unit 34 controls the light-emitting unit 31 to concurrently light the violet LED 31a, the blue LED 31b, the green LED 31c, the amber LED 31d, and the red LED 31e, and then generates a light-emitting state signal according to such control and outputs the signal to the control unit 44. According to such operation of the light source control unit 34, mixed light of the V light, the B light, the G light, the A light, and the R light is allowed to irradiate the desired living organism tissue as the illumination light when the observation distance between the distal end portion 2c and the desired living organism tissue is a distance corresponding to the middle-distance view.

The light source control unit 34 also controls the light-emitting unit 31 to change the light-emission amount EV, the light-emission amount EB, and the light-emission amount EG while maintaining a preset light-emission amount ratio among these light-emission amounts. The light source control unit 34 also controls the light-emitting unit 31 to change the light-emission amount EA inversely with a change in the light-emission amount ER within a range greater than zero and less than a light-emission amount EA2. The light source control unit 34 also controls the light-emitting unit 31 to change the light-emission amount ER inversely with a change in the light-emission amount EA within a range greater than zero and less than a light-emission amount ER1. Note that in the present embodiment, the light-emission amount EA2 is set as an amount of light corresponding to the light-emission amount EG2, and the light-emission amount ER1 is set as an amount of light corresponding to the light-emission amount EG1. Therefore, in the present embodiment, a relationship of EA2>ER1 is satisfied.

More specifically, when the light-emission amount ratio among the light-emission amount EV, the light-emission amount EB, the light-emission amount EG, the light-emission amount EA, and the light-emission amount ER is represented by 1:1:1:α:β (where 0<α<1 and 0<β<1), for example, the light source control unit 34, when receiving the control signal CSA, controls the light-emitting unit 31 to linearly increase the three light-emission amounts EV, EB, and EG while maintaining EV=EB=EG, and linearly decrease the light-emission amount ER while linearly increasing the light-emission amount EA so as to allow an increase rate of the value of α of the light-emission amount ratio to exceed a decrease rate of the value of β (see FIGS. 3 and 4). In addition, when the light-emission amount ratio among the light-emission amount EV, the light-emission amount EB, the light-emission amount EG, the light-emission amount EA, and the light-emission amount ER is represented by 1:1:1:α:β, for example, the light source control unit 34, when receiving the control signal CSB, controls the light-emitting unit 31 to linearly decrease the three light-emission amounts EV, EB, and EG while maintaining EV=EB=EG, and linearly increase the light-emission amount ER while linearly decreasing the light-emission amount EA so as to allow a decrease rate of the value of α of the light-emission amount ratio to exceed an increase rate of the value of β (see FIGS. 3 and 4).

Note that the alternate long and short dash line in FIG. 4 indicates changes in the light-emission amount when EG=EA. Therefore, when the control illustrated in the graph of FIG. 4 is performed, a relationship of EG2=EA2 is satisfied.

The image processing unit 42 performs a process for generating each of the image data IDV, the image data IDB, the image data IDG, the image data IDA, and the image data IDR based on image data outputted from the signal processing unit 41 and a control signal outputted from the control unit 44 according to the aforementioned operation of the light source control unit 34.

The observed image generation unit 43, based on a control signal outputted from the control unit 44, generates an observed image by assigning the image data IDV and the image data IDB outputted from the image processing unit 42 to the B channel of the display device 5, assigning the image data IDG outputted from the image processing unit 42 to the G channel of the display device 5, and assigning the image data IDA and IDR outputted from the image processing unit 42 to the R channel of the display device 5, and then outputs the generated observed image to the display device 5.

According to the aforementioned operation of the present embodiment, when the light-emission amount EG is less than or equal to the light-emission amount EG1, the light source control unit 34 performs a light-emission amount control EL1 on the light-emitting unit 31 to change the light-emission amounts of the blue LED 31b, the green LED 31c, and the red LED 31e so as to allow a color balance of light of each color included in the illumination light supplied from the light source apparatus 3 to the endoscope 2 to be maintained at a color balance CB1. In addition, according to the aforementioned operation of the present embodiment, when the light-emission amount EG is greater than the light-emission amount EG1, the light source control unit 34 performs a light-emission amount control EL2 on the light-emitting unit 31 to change the light-emission amount ER by a method different from the light-emission amount control EL1 while changing the light-emission amounts EB and EG by a method similar to the light-emission amount control EL1 so as to allow the color balance of light of each color included in the illumination light supplied from the light source apparatus 3 to the endoscope 2 to become a color balance CB2 different from the color balance CB1. According to the aforementioned operation of the present embodiment, the light source control unit 34 performs, in the light-emission amount control EL1, a control for setting the light-emission amount EA to zero and a control of gradually increasing the light-emission amounts EB, EG and ER. According to the aforementioned operation of the present embodiment, the light source control unit 34 performs, in the light-emission amount control EL2, a control of gradually increasing the light-emission amounts EB and EG, a control of gradually decreasing the light-emission amount ER to zero, and a control of gradually increasing the light-emission amount EA from zero.

Described next is an operation performed when the current light-emission amount EGC of the green LED 31c is greater than or equal to the light-emission amount EG2, that is, when the observation distance between the distal end portion 2c and the desired living organism tissue is a distance corresponding to a distant view.

The light source control unit 34 controls the light-emitting unit 31 to concurrently light the violet LED 31a, the blue LED 31b, the green LED 31c, and the amber LED 31d while quenching the red LED 31e, and then generates a light-emitting state signal according to such control and outputs the signal to the control unit 44. According to such operation of the light source control unit 34, when the observation distance between the distal end portion 2c and the desired living organism tissue is long a distance corresponding to the distant view, mixed light of the V light, the B light, the G light, and the A light is allowed to irradiate the desired living organism tissue as the illumination light.

The light source control unit 34 also controls the light-emitting unit 31 to change the light-emission amount EV, the light-emission amount EB, the light-emission amount EG, and the light-emission amount EA while maintaining a preset light-emission amount ratio among these light-emission amounts.

More specifically, for example, when the light-emission amount ratio among the light-emission amount EV, the light-emission amount EB, the light-emission amount EG, and the light-emission amount EA is set to 1:1:1:1, the light source control unit 34, when receiving the control signal CSA, controls the light-emitting unit 31 to linearly increase the four light-emission amounts while maintaining EV=EB=EG=EA (see FIG. 4). In addition, for example, when the light-emission amount ratio among the light-emission amount EV, the light-emission amount EB, the light-emission amount EG, and the light-emission amount EA is set to 1:1:1:1, the light source control unit 34, when receiving the control signal CSB, controls the light-emitting unit 31 to linearly decrease the four light-emission amounts while maintaining EV=EB=EG=EA (see FIG. 4).

The image processing unit 42 performs a process for generating each of the image data IDV, the image data IDB, the image data IDG, and the image data IDA based on image data outputted from the signal processing unit 41 and a control signal outputted from the control unit 44 according to the aforementioned operation of the light source control unit 34.

The observed image generation unit 43, based on a control signal outputted from the control unit 44, generates an observed image by assigning the image data IDV and the image data IDB outputted from the image processing unit 42 to the B channel of the display device 5, assigning the image data IDG outputted from the image processing unit 42 to the G channel of the display device 5, and assigning the image data IDA outputted from the image processing unit 42 to the R channel of the display device 5, and then outputs the generated observed image to the display device 5.

Finally, a specific example of a method of setting the light-emission amounts EG1 and EG2 of the present embodiment will be described.

The light-emission amount EG1 is set based on a measurement result obtained by, for example, irradiating living organism tissue with only the R light and actually measuring the light-emission amount ER at which secondary light starts to be generated from the living organism tissue. Therefore, in the example illustrated in FIG. 3, the light-emission amount EG1 is set to the same amount of light as the light-emission amount ER1.

Alternatively, the light-emission amount EG1 is set as a light-emission amount obtained as a result of performing computation using Equations (1) and (2) below.

$$EG1 = EGM \times F(Cp) \quad (1)$$

$$Cp = AVr/AVg \quad (2)$$

EGM in Equation (1) represents a maximum light-emission amount of the G light of the green LED 31c. F(Cp) in Equation (1) represents a value obtained by applying a computed value Cp, which is obtained through computation using Equation (2), to a variable x of a predetermined function F(x). AVr in Equation (2) represents a mean value of absorption coefficients of oxygenated hemoglobin at each wavelength included in the wavelength range of the R light. AVg in Equation (2) represents a mean value of the absorption coefficient of oxygenated hemoglobin at each wavelength included in the wavelength range of the G light. In other words, the computed value Cp of Equation (2) represents a ratio of the mean value AVr to the mean value AVg. According to Equations (1) and (2), the light-emission amount EG1 is set based on the mean value AVg and the mean value AVr.

The light-emission amount EG2 is set based on a measurement result obtained by, for example, irradiating living organism tissue with only the R light and actually measuring the light-emission amount ER at which secondary light starts to be generated from the living organism tissue. Therefore, in the example illustrated in FIG. 4, the light-emission amount EG2 is set to the same amount of light as the light-emission amount ER2.

Alternatively, the light-emission amount EG2 is set as a light-emission amount obtained as a result of performing computation using Equations (3) and (4) below.

$$EG2 = EGM \times F(Cq) \quad (3)$$

$$Cq = AVa/AVg \quad (4)$$

F(Cq) in Equation (3) represents a value obtained by applying a computed value Cq, which is obtained through computation using Equation (4), to a variable x of a predetermined function F(x). AVa in Equation (4) represents a mean value of the absorption coefficients of oxygenated hemoglobin at each wavelength included in the wavelength range of the A light. In other words, the computed value Cq of Equation (4) represents a ratio of the mean value AVa to the mean value AVg. According to Equations (3) and (4), the light-emission amount EG2 is set based on the mean value AVg and the mean value AVa.

Note that according to the present embodiment, each of the computed values Cp and Cq may be obtained by, instead of using the mean value of the absorption coefficients of oxygenated hemoglobin calculated according to the wavelength range of light emitted from the light-emitting unit 31, using a value of a product obtained by multiplying a spectral reflectance of a mucous membrane of the living organism (for example, the mucous membrane of a digestive tract) at a predetermined site in the living organism by a spectral product that is the value indicating an index of a total optical performance of the endoscope system 1. In such a case, it is possible to use as the spectral product a value of a product obtained by, for example, multiplying a spectral intensity of light emitted from the light-emitting unit 31 by the spectral sensitivity of the image pickup device 21b and by the spectral transmittance of each optical member provided on a path from the light-emitting unit 31 to the image pickup device 21b.

When the desired living organism tissue in a subject is irradiated with illumination light in the visible range, a phenomenon may occur such that secondary light is generated due to reflection of the illumination light at a place different from the desired living organism tissue, and the desired living organism tissue is irradiated with the secondary light (together with the illumination light). In addition, considering the light absorption characteristics of hemoglobin, it is estimated that secondary light generated due to the aforementioned phenomenon contains more components on the longer wavelength side (red) in the visible range than components on the shorter wavelength side (blue to green). Therefore, when an image of the desired living organism tissue is picked up while the aforementioned phenomenon occurs, there is a possibility that the color tone of the picked-up image of the desired living organism tissue may differ between the near-view observation and the distant-view observation due to the difference in the amount of secondary light, which irradiates the desired living organism tissue, depending on the observation distance. More specifically, when an image of the desired living organism tissue is picked up while the aforementioned phenomenon occurs, there is a possibility that in the distant-view observation in which the amount of secondary light irradiating the desired living organism tissue is relatively large, for example, an image may be obtained in which the red color appears to be emphasized relative to the color tone of an image obtained in the near-view observation in which the amount of secondary light irradiating the desired living organism tissue is relatively small.

In contrast, according to the aforementioned operation of the light source control unit 34 of the present embodiment, the desired living organism tissue is irradiated with the R light, which is relatively difficult to be absorbed by hemoglobin, in the near-view observation, and the desired living organism tissue is irradiated with the A light, which is relatively easily absorbed by hemoglobin, in the distant-view observation, based on the assumption that there is a positive correlation between the amount of secondary light that irradiates the desired living organism tissue and the amount of the G light that is increased or decreased according to the observation distance for observing the desired living organism tissue. In other words, according to the aforementioned operation of the light source control unit 34 of the present embodiment, the desired living organism tissue is irradiated with the R light, from which secondary light is relatively easily generated, in the period in which the light-emission amount EG is relatively small, and the desired living organism tissue is irradiated with the A light, from which the secondary light is relatively difficult to be generated, in the period in which the light-emission amount EG is relatively large based on the aforementioned estimation. Thus, according to the present embodiment, it is possible to suppress changes in the color tone of an image that would occur depending on the observation distance for observing the desired living organism tissue. Consequently, high accuracy is ensured for diagnosis that is performed based on the color tone of living organism tissue in a subject.

Figure 5:
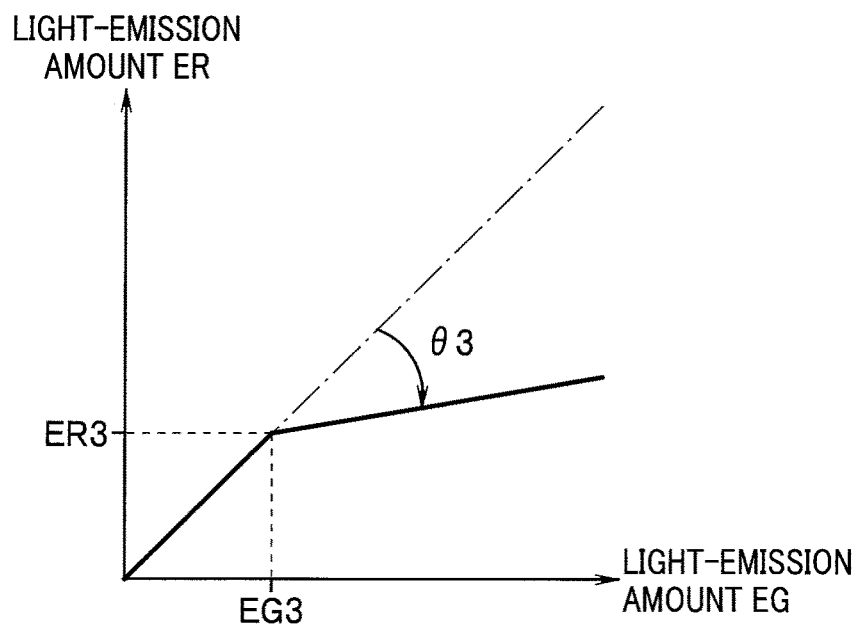
FIG. 5 is a view for illustrating an operation of a light source apparatus according to a first modification of the embodiment.

Note that the light source control unit 34 of the present embodiment is not limited to the one that performs a control as illustrated in the graphs of FIGS. 3 and 4, and may be the one that performs a control as illustrated in the graph of FIG. 5, for example. The operation of such light source control unit 34 and the like according to a first modification of the present embodiment will be described below. In the following description, specific descriptions related to the portions to which the aforementioned operations and the like are applicable are omitted as appropriate. FIG. 5 is a view for illustrating an operation of a light source apparatus according to the first modification of the embodiment.

Described first is an operation performed when the current light-emission amount EGC of the green LED 31c is greater than zero and less than or equal to a light-emission amount EG3, that is, the observation distance between the distal end portion 2c and the desired living organism tissue is a distance corresponding to the near view. A specific example of a method of setting the light-emission amount EG3 will be described later.

The light source control unit 34 controls the light-emitting unit 31 to concurrently light the violet LED 31a, the blue LED 31b, the green LED 31c, and the red LED 31e while quenching the amber LED 31d, and then generates a light-emitting state signal according to such control and outputs the signal to the control unit 44.

The light source control unit 34 also controls the light-emitting unit 31 to change the light-emission amount EV, the light-emission amount EB, the light-emission amount EG, and the light-emission amount ER while maintaining a preset light-emission amount ratio among these light-emission amounts.

More specifically, for example, when the light-emission amount ratio among the light-emission amount EV, the light-emission amount EB, the light-emission amount EG, and the light-emission amount ER is set to 1:1:1:1, the light source control unit 34, when receiving the control signal CSA, controls the light-emitting unit 31 to linearly increase the four light-emission amounts while maintaining EV=EB=EG=ER (see FIG. 5). In addition, for example, when the light-emission amount ratio among the light-emission amount EV, the light-emission amount EB, the light-emission amount EG, and the light-emission amount ER is set to 1:1:1:1, the light source control unit 34, when receiving the control signal CSB, controls the light-emitting unit 31 to linearly decrease the four light-emission amounts while maintaining EV=EB=EG=ER (see FIG. 5).

The image processing unit 42 performs a process for generating each of the image data IDV, the image data IDB, the image data IDG, and the image data IDR based on image data outputted from the signal processing unit 41 and a control signal outputted from the control unit 44 according to the aforementioned operation of the light source control unit 34.

The observed image generation unit 43, based on a control signal outputted from the control unit 44, generates an observed image by assigning the image data IDV and the image data IDB outputted from the image processing unit 42 to the B channel of the display device 5, assigning the image data IDG outputted from the image processing unit 42 to the G channel of the display device 5, and assigning the image data IDR outputted from the image processing unit 42 to the R channel of the display device 5, and then outputs the generated observed image to the display device 5.

Described next is an operation performed when the current light-emission amount EGC of the green LED 31c is greater than the light-emission amount EG3, that is, when the observation distance between the distal end portion 2c and the desired living organism tissue is a distance corresponding to the middle-distance view or the distant view.

The light source control unit 34 controls the light-emitting unit 31 to concurrently light the violet LED 31a, the blue LED 31b, the green LED 31c, and the red LED 31e while quenching the amber LED 31d, and then generates a light-emitting state signal according to such control and outputs the signal to the control unit 44. In other words, in the present modification, mixed light of the V light, the B light, the G light, and the R light is allowed to irradiate the desired living organism tissue as the illumination light regardless of the observation distance between the distal end portion 2c and the desired living organism tissue.

The light source control unit 34 also controls the light-emitting unit 31 to change the light-emission amount EV, the light-emission amount EB, and the light-emission amount EG while maintaining a preset light-emission amount ratio among these light-emission amounts. In addition, the light source control unit 34, when detecting that the light-emission amount ER is greater than a light-emission amount ER3 set in advance as the amount of light corresponding to the light-emission amount EG3, controls the light-emitting unit 31 to change the light-emission amount ER at a change rate different from the change rate for changing the light-emission amount EG.

More specifically, when the light-emission amount ratio among the light-emission amount EV, the light-emission amount EB, the light-emission amount EG, and the light-emission amount ER is represented by 1:1:1:γ (where 0<γ<1), for example, the light source control unit 34, when receiving the control signal CSA, controls the light-emitting unit 31 to linearly increase the three light-emission amounts EV, EB, and EG while maintaining EV=EB=EG, and linearly increase the light-emission amount ER at an increase rate smaller than the increase rate of the light-emission amount EG so as to allow the value of y of the light-emission amount ratio to become gradually smaller (see FIG. 5). In addition, when the light-emission amount ratio among the light-emission amount EV, the light-emission amount EB, the light-emission amount EG, and the light-emission amount ER is represented by 1:1:1: γ, for example, the light source control unit 34, when receiving the control signal CSB, controls the light-emitting unit 31 to linearly decrease the three light-emission amounts EV, EB, and EG while maintaining EV=EB=EG and linearly decrease the light-emission amount ER at a decrease rate smaller than the decrease rate of the light-emission amount EG so as to allow the value of y of the light-emission amount ratio to become gradually greater (see FIG. 5).

Note that the alternate long and short dash line in FIG. 5 indicates changes in the light-emission amount when EG=ER. Therefore, when the control illustrated in the graph of FIG. 5 is performed, the relationship of EG3=ER3 is satisfied. In FIG. 5, θ3 corresponds to the angle indicating the difference between the change rate of the light-emission amount ER when the light-emission amount EG is less than or equal to the light-emission amount EG3 and the change rate of the light-emission amount ER when the light-emission amount EG is greater than the light-emission amount EG3, and is set using a method described below.

The image processing unit 42 performs a process for generating each of the image data IDV, the image data IDB, the image data IDG, and the image data IDR based on image data outputted from the signal processing unit 41 and a control signal outputted from the control unit 44 according to the aforementioned operation of the light source control unit 34.

The observed image generation unit 43, based on a control signal outputted from the control unit 44, generates an observed image by assigning the image data IDV and the image data IDB outputted from the image processing unit 42 to the B channel of the display device 5, assigning the image data IDG outputted from the image processing unit 42 to the G channel of the display device 5, and assigning the image data IDR outputted from the image processing unit 42 to the R channel of the display device 5, and then outputs the generated observed image to the display device 5.

According to the aforementioned operation of the present modification, when the light-emission amount EG is less than or equal to the light-emission amount EG3, the light source control unit 34 performs a light-emission amount control EL3 on the light-emitting unit 31 to change the light-emission amounts of the violet LED 31*a*, the blue LED 31*b*, the green LED 31*c*, and the red LED 31*e* so as to allow the color balance of light of each color included in the illumination light supplied from the light source apparatus 3 to the endoscope 2 to be maintained at a color balance CB3. In addition, according to the aforementioned operation of the present modification, when the light-emission amount EG is greater than the light-emission amount EG3, the light source control unit 34 performs a light-emission amount control EL4 on the light-emitting unit 31 to change the light-emission amount ER by a method different from the light-emission amount control EL3 while changing the light-emission amount EV and the light-emission amounts EB and EG by a method similar to the light-emission amount control EL3 so as to allow the color balance of light of each color included in the illumination light supplied from the light source apparatus 3 to the endoscope 2 to become a color balance CB4 different from the color balance CB3. According to the aforementioned operation of the present modification, the light source control unit 34 performs, in the light-emission amount control EL3, a control for setting the light-emission amount EA to zero and a control of gradually increasing the light-emission amount EV and the light-emission amounts EB, EG and ER at an increase rate ZA. According to the aforementioned operation of the present modification, the light source control unit 34 performs, in the light-emission amount control EL4, a control of gradually increasing the light-emission amount EV and the light-emission amounts EB and EG at the increase rate ZA and a control of gradually increasing the light-emission amount ER at an increase rate ZB smaller than the increase rate ZA. Note that the increase rate ZA is represented as, in the graph of FIG. 5, the magnitude of the slope of the straight line in the portion where the light-emission amount EG is less than or equal to the light-emission amount EG3, for example. The increase rate ZB is represented as, in the graph of FIG. 5, the magnitude of the slope of the straight line in the portion where the light-emission amount EG is greater than the light-emission amount EG3, for example.

Finally, a specific example of a method of setting the light-emission amount EG3 and the angle θ3 in the present modification will be described.

The light-emission amount EG3 is set based on the measurement result obtained by, for example, irradiating living organism tissue with only the R light and actually measuring the light-emission amount ER at which secondary light starts to be generated from the living organism tissue. Therefore, in the example illustrated in FIG. 5, the light-emission amount EG3 is set to the same amount of light as the light-emission amount ER3. When the light-emission amount EG3 is set using such a method, the angle θ3 is set based on the measurement result obtained by, for example, concurrently irradiating the living organism tissue with the G light emitted from the green LED 31*c* to which the maximum light-emission amount EGM is set and the R light emitted from the red LED 31*e* to which a given light-emission amount ER is set, and actually measuring the light-emission amount ER at which secondary light emitted from the living organism tissue is reduced.

Alternatively, the light-emission amount EG3 is set as a light-emission amount obtained as a result of performing computation using Equations (5) and (6) below.

$$EG3 = EGM \times G(Cr) \tag{5}$$

$$Cr = AVr/AVg \tag{6}$$

G(Cr) in Equation (5) represents the value obtained by applying a computed value Cr, which is obtained through computation using Equation (6), to a variable x of a predetermined function G(x). The computed value Cr of Equation (6) can be calculated with the same method as the method for the computed value Cp of Equation (2). In other words, the computed value Cr of Equation (6) represents the ratio of the mean value AVr to the mean value AVg. According to Equations (5) and (6), the light-emission amount EG3 is set based on the mean value AVg and the mean value AVr. When the light-emission amount EG3 is set using such a method, the angle θ3 is set as the value obtained by, for example, applying the computed value Cr, which is obtained through computation using Equation (6), to a variable t of a predetermined function I(t).

Note that according to the present modification, the computed value Cr may be obtained by, instead of using the mean value of the absorption coefficient of oxygenated hemoglobin calculated according to the wavelength range of light emitted from the light-emitting unit 31, using the value of a product obtained by multiplying the spectral reflectance of the mucous membrane of the living organism (for example, the mucous membrane of a digestive tract) at a predetermined site in the living organism by a spectral product that is the value indicating the index of the total optical performance of the endoscope system 1. In such a case, it is possible to use as the spectral product the value of a product obtained by, for example, multiplying the spectral intensity of light emitted from the light-emitting unit 31 by the spectral sensitivity of the image pickup device 21*b* and by the spectral transmittance of each optical member provided on a path from the light-emitting unit 31 to the image pickup device 21*b*.

According to the aforementioned operation of the light source control unit 34 of the present modification, the change rate of the amount of the R light that irradiates the desired living organism tissue during the middle-distance view to the distant-view observation (i.e., the period in which the light-emission amount EG is relatively large) is set smaller than the change rate of the amount of the R light that irradiates the desired living organism tissue during the near-view observation (i.e., the period in which the light-emission amount EG is relatively small) based on the assumption that there is a positive correlation between the amount of secondary light that irradiates the desired living organism tissue and the amount of the G light that is increased or decreased according to the observation distance for observing the desired living organism tissue. Thus, according to the present modification, it is possible to suppress changes in the color tone of an image that would occur depending on the observation distance for observing the desired living organism tissue. Consequently, high accuracy is ensured for diagnosis that is performed based on the color tone of living organism tissue in a subject.

Figure 6:
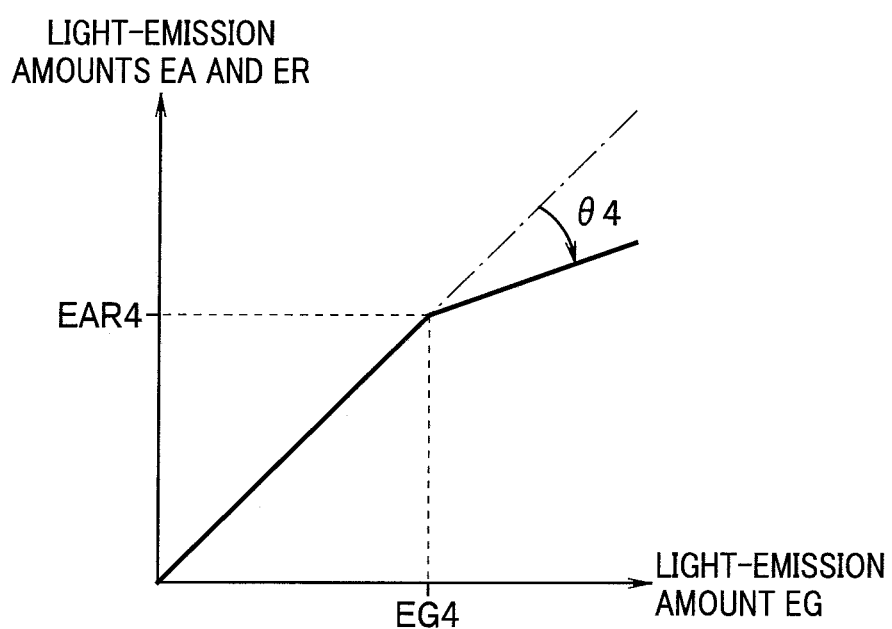
FIG. 6 is a view for illustrating an operation of a light source apparatus according to a second modification of the embodiment.

Note that the light source control unit 34 of the present embodiment is not limited to the one that performs a control as illustrated in the graphs of FIGS. 3 and 4, and may be the one that performs a control as illustrated in the graph of FIG. 6, for example. The operation of such light source control unit 34 and the like according to a second modification of the present embodiment will be described below. FIG. 6 is a view for illustrating the operation of a light source apparatus according to the second modification of the embodiment.

Described first is an operation performed when the current light-emission amount EGC of the green LED 31c is greater than zero and less than or equal to a light-emission amount EG4, that is, when the observation distance between the distal end portion 2c and the desired living organism tissue is a distance corresponding to the near view or the middle-distance view. A specific example of a method of setting the light-emission amount EG4 will be described later.

The light source control unit 34 controls the light-emitting unit 31 to concurrently light the violet LED 31a, the blue LED 31b, the green LED 31c, the amber LED 31d, and the red LED 31e, and then generates a light-emitting state signal according to such control and outputs the signal to the control unit 44.

The light source control unit 34 also controls the light-emitting unit 31 to change the light-emission amount EV, the light-emission amount EB, the light-emission amount EG, the light-emission amount EA, and the light-emission amount ER while maintaining a preset light-emission amount ratio among these light-emission amounts.

More specifically, for example, when the light-emission amount ratio among the light-emission amount EV, the light-emission amount EB, the light-emission amount EG, the light-emission amount EA, and the light-emission amount ER is set to 1:1:1:1:1, the light source control unit 34, when receiving the control signal CSA, controls the light-emitting unit 31 to linearly increase the five light-emission amounts while maintaining EV=EB=EG=EA=ER (see FIG. 6). In addition, for example, when the light-emission amount ratio among the light-emission amount EV, the light-emission amount EB, the light-emission amount EG, the light-emission amount EA, and the light-emission amount ER is set to 1:1:1:1:1, the light source control unit 34, when receiving the control signal CSB, controls the light-emitting unit 31 to linearly decrease the five light-emission amounts while maintaining EV=EB=EG=EA=ER (see FIG. 6).

The image processing unit 42 performs a process for generating each of the image data IDV, the image data IDB, the image data IDG, the image data IDA, and the image data IDR based on image data outputted from the signal processing unit 41 and a control signal outputted from the control unit 44 according to the aforementioned operation of the light source control unit 34.

The observed image generation unit 43, based on a control signal outputted from the control unit 44, generates an observed image by assigning the image data IDV and the image data IDB outputted from the image processing unit 42 to the B channel of the display device 5, assigning the image data IDG outputted from the image processing unit 42 to the G channel of the display device 5, and assigning the image data IDA and IDR outputted from the image processing unit 42 to the R channel of the display device 5, and then outputs the generated observed image to the display device 5.

Described next is an operation performed when the current light-emission amount EGC of the green LED 31c is greater than the light-emission amount EG4, that is, when the observation distance between the distal end portion 2c and the desired living organism tissue is a distance corresponding to the distant view.

The light source control unit 34 controls the light-emitting unit 31 to concurrently light the violet LED 31a, the blue LED 31b, the green LED 31c, the amber LED 31d, and the red LED 31e, and then generates a light-emitting state signal according to such control and outputs the signal to the control unit 44. In other words, in the present modification, mixed light of the V light, the B light, the G light, the A light, and the R light is allowed to irradiate the desired living organism tissue as the illumination light regardless of the observation distance between the distal end portion 2c and the desired living organism tissue.

The light source control unit 34 also controls the light-emitting unit 31 to change the light-emission amount EV, the light-emission amount EB, and the light-emission amount EG while maintaining a preset light-emission amount ratio among these light-emission amounts. In addition, the light source control unit 34, when detecting that the light-emission amount EA and the light-emission amount ER are greater than a light-emission amount EAR4 set in advance as the amount of light corresponding to the light-emission amount EG4, controls the light-emitting unit 31 to change the light-emission amount EA and the light-emission amount ER at a change rate different from the change rate for changing the light-emission amount EG.

More specifically, when the light-emission amount ratio among the light-emission amount EV, the light-emission amount EB, the light-emission amount EG, the light-emission amount EA, and the light-emission amount ER is represented by 1:1:1:$\delta$:$\delta$ (where 0<$\delta$<1), for example, the light source control unit 34, when receiving the control signal CSA, controls the light-emitting unit 31 to linearly increase the three light-emission amounts EV, EB, and EG while maintaining EV=EB=EG and linearly increase the light-emission amount EA and the light-emission amount ER at an increase rate smaller than the increase rate of the light-emission amount EG so as to allow the value of $\delta$ of the light-emission amount ratio to become gradually smaller (see FIG. 6). In addition, when the light-emission amount ratio among the light-emission amount EV, the light-emission amount EB, the light-emission amount EG, the light-emission amount EA, and the light-emission amount ER is represented by 1:1:1:$\delta$:$\delta$, for example, the light source control unit 34, when receiving the control signal CSB, controls the light-emitting unit 31 to linearly decrease the three light-emission amounts EV, EB, and EG while maintaining EV=EB=EG, and linearly decrease the light-emission amount EA and the light-emission amount ER at a decrease rate smaller than the decrease rate of the light-emission amount EG so as to allow the value of $\delta$ of the light-emission amount ratio to become gradually greater (see FIG. 6).

Note that the alternate long and short dash line in FIG. 6 indicates changes in the light-emission amount when EG=EA=ER. Therefore, when the control illustrated in the graph of FIG. 6 is performed, the relationship of EG4=EAR4 is satisfied. In FIG. 6, $\theta$4 corresponds to the angle indicating the difference between the change rate of the light-emission amounts EA and ER when the light-emission amount EG is less than or equal to the light-emission amount EG4 and the change rate of the light-emission amounts EA and ER when the light-emission amount EG is greater than the light-emission amount EG4, and is set using a method described below.

According to the present modification, regarding the red components that are included in a picked-up image of the desired living organism tissue due to the irradiation of the desired living organism tissue with illumination light including the A light and the R light, the proportion of the components derived from secondary light can be reduced than in the first modification. Therefore, the relationship of EG3<EG4 is satisfied between the light-emission amount EG3 of the first modification and the light-emission amount EG4 of the present modification.

In addition, the relationship of θ3>θ4 is satisfied between the angle θ3 of the first modification and the angle θ4 of the present modification. In other words, the increase rate of the light-emission amounts EA and ER (which corresponds to an increase rate ZC described below) in the control performed when the light-emission amount EGC is greater than the light-emission amount EG4 is greater than the increase rate of the light-emission amount ER (which corresponds to the increase rate ZB described in the first modification) in the control performed when the light-emission amount EGC is greater than the light-emission amount EG3.

The image processing unit 42 performs a process for generating each of the image data IDV, the image data IDB, the image data IDG, the image data IDA, and the image data IDR based on image data outputted from the signal processing unit 41 and a control signal outputted from the control unit 44 according to the aforementioned operation of the light source control unit 34.

The observed image generation unit 43, based on a control signal outputted from the control unit 44, generates an observed image by assigning the image data IDV and the image data IDB outputted from the image processing unit 42 to the B channel of the display device 5, assigning the image data IDG outputted from the image processing unit 42 to the G channel of the display device 5, and assigning the image data IDA and IDR outputted from the image processing unit 42 to the R channel of the display device 5, and then outputs the generated observed image to the display device 5.

According to the aforementioned operation of the present modification, when the light-emission amount EG is less than or equal to the light-emission amount EG4, the light source control unit 34 performs a light-emission amount control EL5 on the light-emitting unit 31 to change the light-emission amounts of the violet LED 31a, the blue LED 31b, the green LED 31c, the amber LED 31d, and the red LED 31e so as to allow the color balance of light of each color included in the illumination light supplied from the light source apparatus 3 to the endoscope 2 to be maintained at a color balance CB5. In addition, according to the aforementioned operation of the present modification, when the light-emission amount EG is greater than the light-emission amount EG3, the light source control unit 34 performs a light-emission amount control EL6 on the light-emitting unit 31 to change the light-emission amounts EA and ER by a method different from the light-emission amount control EL5 while changing the light-emission amount EV and the light-emission amounts EB and EG by a method similar to the light-emission amount control EL5 so as to allow the color balance of light of each color included in the illumination light supplied from the light source apparatus 3 to the endoscope 2 to become a color balance CB6 different from the color balance CB5. According to the aforementioned operation of the present modification, the light source control unit 34 performs, in the light-emission amount control EL5, a control of gradually increasing the light-emission amounts EV, EB, EG, EA and ER at the increase rate ZA. According to the aforementioned operation of the present modification, the light source control unit 34 performs, in the light-emission amount control EL6, a control of gradually increasing the light-emission amount EV and the light-emission amounts EB and EG at the increase rate ZA and a control of gradually increasing the light-emission amounts EA and ER at the increase rate ZC smaller than the increase rate ZA and greater than the increase rate ZB. Note that the increase rate ZC is represented as, in the graph of FIG. 6, the magnitude of the slope of the straight line in the portion where the light-emission amount EG is greater than the light-emission amount EG4, for example.

Finally, a specific example of a method of setting the light-emission amount EG4 and angle θ4 in the present modification will be described.

The light-emission amount EG4 is set based on the measurement result obtained by, for example, irradiating living organism tissue with the A light and the R light and actually measuring one of the light-emission amount EA or ER at which secondary light starts to be generated from the living organism tissue. Therefore, in the example illustrated in FIG. 6, the light-emission amount EG4 is set to the light-emission amount EAR4. When the light-emission amount EG4 is set using such a method, the angle θ4 is set based on the measurement result obtained by, for example, concurrently irradiating the living organism tissue with the G light emitted from the green LED 31c to which the maximum light-emission amount EGM is set, the A light emitted from the amber LED 31d to which a given light-emission amount EA is set, and the R light emitted from the red LED 31e to which a given light-emission amount ER is set, and actually measuring one of the light-emission amount EA or ER at which secondary light emitted from the living organism tissue is reduced.

Alternatively, the light-emission amount EG4 is set as a light-emission amount obtained as a result of performing computation using Equations (7) and (8) below.

$$EG4 = EGM \times H(Cs) \qquad (7)$$

$$Cs = [(\alpha \Delta AVa + \beta \times AVr)/(\alpha + \beta)]/AVg \qquad (8)$$

H(Cs) in Equation (7) represents the value obtained by applying a computed value Cs, which is obtained through computation using Equation (8), to a variable x of a predetermined function H(x). Each of α and β in Equation (8) represents a predetermined constant greater than zero. In other words, the computed value Cs of Equation (8) represents the ratio of the weighted mean value of the mean values AVa and AVr to the mean value AVg. According to Equations (7) and (8), the light-emission amount EG4 is set based on the mean value AVg, the mean value AVa, and the mean value AVr. When the light-emission amount EG4 is set using such a method, the angle θ4 is set as the value obtained by, for example, applying the computed value Cs, which is obtained through computation using Equation (8), to a variable t of a predetermined function I(t).

Note that according to the present modification, the computed value Cs may be obtained by, instead of using the mean value of the absorption coefficients of oxygenated hemoglobin calculated according to the wavelength range of light emitted from the light-emitting unit 31, using the value of a product obtained by multiplying the spectral reflectance of the mucous membrane of the living organism (for example, the mucous membrane of a digestive tract) at a predetermined site in the living organism by a spectral product that is the value indicating the index of the total optical performance of the endoscope system 1. In such a case, it is possible to use as the spectral product the value of a product obtained by, for example, multiplying the spectral intensity of light emitted from the light-emitting unit 31 by the spectral sensitivity of the image pickup device 21b and by the spectral transmittance of each optical member provided on a path from the light-emitting unit 31 to the image pickup device 21b.

According to the aforementioned operation of the light source control unit 34 of the present modification, the change rate of the amount of each of the A light and the R light that irradiates the desired living organism tissue during the distant-view observation (i.e., the period in which the light-emission amount EG is relatively large) is set smaller than the change rate of the amount of each of the A light and the R light that irradiates the desired living organism tissue during the near view to the middle-distance view observation (i.e., the period in which the light-emission amount EG is relatively small) based on the assumption that there is a positive correlation between the amount of secondary light that irradiates the desired living organism tissue and the amount of the G light that is increased or decreased according to the observation distance for observing the desired living organism tissue. Thus, according to the present modification, it is possible to suppress changes in the color tone of an image that would occur depending on the observation distance for observing the desired living organism tissue. Consequently, high accuracy is ensured for diagnosis that is performed based on the color tone of living organism tissue in a subject.

In the aforementioned two modifications, a light-emission amount control is performed that suppresses changes in the color tone of an image that would occur due to secondary light generated from an object during the distant-view observation, based on the color tone of a picked-up image of return light generated from the object during the near-view observation. On the contrary, it is also possible to appropriately modify the aforementioned two modifications and perform, for example, a light-emission amount control of, based on the color tone of a picked-up image of return light and secondary light generated from an object during the distant-view observation, changing the color tone of an image during the near-view observation so that the secondary light is taken into consideration for the color tone.

More specifically, as the light-emission amount control of the first modification, for example, it is possible to perform a control for, when the light-emission amount EG is greater than a light-emission amount EGX1, changing the light-emission amount ER at the same proportion as the proportion of the light-emission amount EG, and perform a control for, when the light-emission amount EG is less than or equal to the light-emission amount EGX1, changing the light-emission amount ER to become greater than the light-emission amount EG. In addition, as the light-emission amount control of the second modification, for example, it is possible to perform a control for, when the light-emission amount EG is greater than a light-emission amount EGX2, changing each of the light-emission amounts ER and EA at the same proportion as the proportion of the light-emission amount EG, and perform a control for, when the light-emission amount EG is less than or equal to the light-emission amount EGX2, changing each of the light-emission amounts ER and EA to become greater than the light-emission amount EG.

The present invention is not limited to the aforementioned embodiments or modifications, and it goes without saying that the present invention can be changed or applied in a various ways within the spirit and scope of the invention.

What is claimed is:

1. A light source apparatus for endoscope, comprising:
a first light source configured to generate blue light included in illumination light for irradiating living organism tissue in a subject;
a second light source configured to generate green light included in the illumination light;
a third light source configured to generate red light included in the illumination light; and
a light source controller configured to individually control a light-emitting state of each of the first light source, the second light source, and the third light source,
wherein the light source controller is configured to:
when a light-emission amount of the second light source is less than or equal to a predetermined light-emission amount, perform a first light-emission amount control of changing a light-emission amount of the first light source, the light-emission amount of the second light source, and a light-emission amount of the third light source so as to allow a color balance of light of each color included in the illumination light to be maintained at a predetermined color balance, and
when the light-emission amount of the second light source is greater than the predetermined light-emission amount, perform a second light-emission amount control of changing the light-emission amount of the third light source by a method different from the first light-emission amount control while changing the light-emission amount of the first light source and the light-emission amount of the second light source by a method similar to the first light-emission amount control so as to allow the color balance of light of each color included in the illumination light to be different from the predetermined color balance;
wherein
in the first light-emission amount control, the light source controller performs a control of gradually increasing the light-emission amount of each of the first light source, the second light source, and the third light source at a first increase rate, and
in the second light-emission amount control, the light source controller performs a control of gradually increasing the light-emission amount of each of the first light source and the second light source at the first increase rate, and a control of gradually increasing the light-emission amount of the third light source at a second increase rate smaller than the first increase rate.

2. The light source apparatus for endoscope according to claim 1, further comprising a fourth light source configured to generate amber light included in the illumination light,
wherein the light source controller is further configured to:
in the first light-emission amount control, perform a control of setting a light-emission amount of the fourth light source to zero, and a control of gradually increasing the light-emission amount of each of the first light source, the second light source, and the third light source, and
in the second light-emission amount control, perform a control of gradually increasing the light-emission amount of each of the first light source and the second light source, a control of gradually decreasing the light-emission amount of the third light source to zero, and a control of gradually increasing the light-emission amount of the fourth light source from zero.

3. The light source apparatus for endoscope according to claim 1, further comprising a fourth light source configured to generate amber light included in the illumination light, wherein the light source controller is further configured to:
   in the first light-emission amount control, perform a control of gradually increasing a light-emission amount of the fourth light source at the first increase rate, and
   in the second light-emission amount control, perform a control of gradually increasing the light-emission amount of each of the third light source and the fourth light source at a third increase rate smaller than the first increase rate and larger than the second increase rate, instead of performing the control of gradually increasing the light-emission amount of the third light source at the second increase rate.

4. The light source apparatus for endoscope according to claim 1, wherein the predetermined light-emission amount is set based on a mean value of absorption coefficients of oxygenated hemoglobin at each wavelength included in a wavelength range of the green light and a mean value of absorption coefficients of oxygenated hemoglobin at each wavelength included in a wavelength range of the red light.

5. The light source apparatus for endoscope according to claim 1, further comprising a fourth light source configured to generate amber light included in the illumination light, wherein the predetermined light-emission amount is set based on a mean value of absorption coefficients of oxygenated hemoglobin at each wavelength included in a wavelength range of the green light, a mean value of absorption coefficients of oxygenated hemoglobin at each wavelength included in a wavelength range of the red light, and a mean value of absorption coefficients of oxygenated hemoglobin at each wavelength included in a wavelength range of the amber light.

6. A light-emission amount control method for a light source apparatus for endoscope, the method being adapted to individually control light-emitting states of a first light source configured to generate blue light included in illumination light for irradiating living organism tissue in a subject, a second light source configured to generate green light included in the illumination light, and a third light source configured to generate red light included in the illumination light, the method comprising:
   performing, when a light-emission amount of the second light source is less than or equal to a predetermined light-emission amount, a first light-emission amount control of changing a light-emission amount of the first light source, the light-emission amount of the second light source, and a light-emission amount of the third light source so as to allow a color balance of light of each color included in the illumination light to be maintained at a predetermined color balance,
   performing, when the light-emission amount of the second light source is greater than the predetermined light-emission amount, a second light-emission amount control of changing the light-emission amount of the third light source by a method different from the first light-emission amount control while changing the light-emission amount of each of the first light source and the second light source by a method similar to the first light-emission amount control so as to allow the color balance of light of each color included in the illumination light to become a color balance different from the predetermined color balance;
   performing, in the first light-emission amount control, a control of gradually increasing the light-emission amount of each of the first light source, the second light source, and the third light source at a first increase rate; and
   performing, in the second light-emission amount control, a control of gradually increasing the light-emission amount of each of the first light source and the second light source at the first increase rate and a control of gradually increasing the light-emission amount of the third light source at a second increase rate smaller than the first increase rate.

7. The light-emission amount control method for the light source apparatus for endoscope according to claim 6, further comprising:
   individually controlling a light-emitting state of a fourth light source, the fourth light source being configured to generate amber light included in the illumination light,
   performing, in the first light-emission amount control, a control of setting a light-emission amount of the fourth light source to zero, and a control of gradually increasing the light-emission amount of each of the first light source, the second light source, and the third light source, and
   performing, in the second light-emission amount control, a control of gradually increasing the light-emission amount of each of the first light source and the second light source, a control of gradually decreasing the light-emission amount of the third light source to zero, and a control of gradually increasing the light-emission amount of the fourth light source from zero.

* * * * *